United States Patent
Campbell et al.

(12) 
(10) Patent No.: US 6,773,731 B2
(45) Date of Patent: Aug. 10, 2004

(54) LIQUID EGG YOLK PRODUCT COMPRISING LYSOPHOSPHOLIPOPROTEIN

(76) Inventors: James S. Campbell, 29834 Burgess Avenue, Mt. Lehman, British Columbia (CA), V4X 2G6; Derk W. te Bokkel, 44876 Iris Place, Chilliwack, British Columbia (CA), V2R 3H6; Kristen D. Thatcher, 6223 192 Street, Surrey, British Columbia (CA), V3S 8E1

( * ) Notice: Subject to any disclaimer, the term of this patent is extended or adjusted under 35 U.S.C. 154(b) by 21 days.

(21) Appl. No.: 10/272,927

(22) Filed: Oct. 18, 2002

(65) Prior Publication Data

US 2004/0076717 A1 Apr. 22, 2004

(51) Int. Cl.$^7$ .............................. A23B 5/16; A23L 1/32
(52) U.S. Cl. ........................................ 426/47; 426/614
(58) Field of Search .......................... 426/47, 614, 568, 426/605; 435/198

(56) References Cited

U.S. PATENT DOCUMENTS

| | | | |
|---|---|---|---|
| 4,034,124 A | 7/1977 | Van Dam | 426/602 |
| 4,119,564 A | 10/1978 | Van Dam | 252/312 |
| 5,028,447 A | 7/1991 | Schenk | 426/605 |
| 5,082,674 A | 1/1992 | Carrell et al. | 426/52 |
| 5,213,968 A | 5/1993 | Castle et al. | 435/68.1 |
| 5,314,706 A | 5/1994 | Colarow et al. | 426/605 |
| 5,378,623 A | 1/1995 | Hattori et al. | 435/198 |
| 5,521,080 A | 5/1996 | Hattori et al. | 435/198 |
| 5,538,874 A | 7/1996 | Hattori et al. | 435/128 |
| 5,750,164 A | 5/1998 | Saito et al. | 426/47 |
| 6,140,094 A | 10/2000 | Loffler et al. | 435/198 |

FOREIGN PATENT DOCUMENTS

| | | | |
|---|---|---|---|
| CA | 2026447 | 3/1991 | A23J/7/00 |
| CA | 1310224 | 11/1992 | A23L/1/24 |
| EP | 0 319 064 B1 | 5/1992 | A23L/1/24 |
| EP | 0 414 024 B1 | 12/1992 | A23L/1/32 |
| EP | 0 575 133 B | 12/1993 | C12N/9/16 |
| GB | 1525929 | 9/1978 | C07G/7/00 |
| GB | 1585105 | 2/1981 | A23J/7/02 |
| JP | 58212783 | 12/1983 | C12N/2/20 |
| JP | 62262998 A2 | 11/1987 | C12P/9/00 |
| JP | 63209742 A2 | 8/1988 | B01F/17/14 |
| JP | 06153939 | 6/1994 | C12N/9/16 |

*Primary Examiner*—Keith Hendricks
(74) *Attorney, Agent, or Firm*—Oyen Wiggs Green & Mutala (57) ABSTRACT

This invention pertains to a novel liquid egg yolk product which contains lysophospholipoprotein. More particularly, this invention pertains to a novel liquid egg yolk product containing lysophospholipoprotein from a phospholipoprotein modified using a non-animal derived phospholipase A, and a process therefor, which is kosher, does not have a porcine or bovine source, and does not contain appreciable levels of amylase. The product is useful as an emulsifier in foodstuffs such as sauces, spreads, mayonnaise, dressings, salad dressings, and the like. A process for the manufacture of a liquid egg yolk product containing lysophospholipoprotein comprising: (a) processing a phospholipase A-containing microbial fermentate to remove undesirable amylase and protease co-products of the fermentation to produce a refined phospholipase A-containing microbial product; and (b) modifying a liquid egg yolk with the refined phospholipase A-containing microbial product of step (a) to produce a modified liquid egg yolk product containing lysophospholipoprotein, said modified liquid egg yolk product having (i) a degree of conversion of phospholipoprotein to lysophospholipoprotein of at least 10%; and (ii) an amylase activity of less than 50 units/litre.

37 Claims, 7 Drawing Sheets

LIQUID EGG YOLK PRODUCT COMPRISING LYSOPHOSPHOLIPOPROTEIN

FIELD OF THE INVENTION

This invention pertains to a novel liquid egg yolk product which contains lysophospholipoprotein. More particularly, this invention pertains to a novel liquid egg yolk product containing lysophospholipoprotein from a phospholipoprotein modified using a non-animal derived phospholipase A, and a process therefor, which is kosher, does not have a porcine or bovine source, and does not contain appreciable levels of amylase. The product is useful as an emulsifier in foodstuffs such as sauces, spreads, mayonnaise, dressings, salad dressings, and the like.

BACKGROUND OF THE INVENTION

Phospholipases are enzymes which act on phospholipids which are found in animal and vegetable cells. Phospholipases are selective enzymes which are classified according to their site of action in the phospholipid molecule. Thus, a phospholipase A1 hydrolyzes the bond between the fatty acid and the glycerine residue at the 1-position of the phospholipid.

The hydrolysis of a phospholipid by a phospholipase results in the production of a "lysophospholipid". Although phospholipids have many industrial uses, lysophospholipids have been shown to be particularly suitable for certain industrial applications. Lysophospholipids have a high solubility in water and this property gives them enhanced emulsification properties in oil/water emulsions. Lysophospholipids have an ability to form emulsions which are reasonably stable to changing pH conditions, including acid conditions, and they are resistant to changing temperatures. The ability of the lysophospholipid to form an oil-water or water-oil emulsion is not reduced by the presence of ions, such as magnesium or calcium ions.

The foregoing properties of the lysophospholipids make them particularly desirable for use in the food, cosmetics and pharmaceutical industries. It has been demonstrated that the conversion of a phospholipid to a lysophospholipid in a phospholipid containing substance, such as a food product, generally leads to an improvement in the stability of that substance.

The most commonly used phospholipase in the industrial hydrolysis of phospholipids is pancreatin, which is an enzyme prepared from the pancreas of pigs. Enzymatic hydrolysis of a phospholipid, using a phospholipase isolated from a micro-organism is, however, known. Such hydrolysis using a phospholipase A is described, for example, in Japanese Unexamined Patent Publication No. Sho-58-212783, and the hydrolysis using a lipase is described in Japanese Unexamined Patent Publication No. Sho63-42691. Furthermore, the enzyme Taka-Diastaseh™, which was isolated from a species of Aspergillus, *A. oryzae*, [Biochem. Z., 261 (1933) 275], has demonstrated a lipase activity which is capable of hydrolyzing a phospholipid. The enzymes isolated from microorganisms have been shown to have less activity than porcine pancreatic enzyme. Moreover, the microorganisms produce amylase and protease as by-products, which are undesirable because they break down starch and proteins and lead to emulsion instability.

Although pancreatin has better properties than enzymes isolated from microorganisms, hydrolysis of a phospholipid using pancreatin has many disadvantages. Firstly, it may be necessary to make continual adjustments to the pH of the reaction mixture during hydrolysis of a phospholipid substrate with porcine pancreatin. The optimum pH for activity of pancreatin is in the range from neutral to weakly alkaline. During the hydrolysis reaction, however, the release of free fatty acids causes the pH to drop, that is, it increases the acidity of the reaction mixture, so that unless counter action is taken, the mixture will become acidic, and therefore outside the pH range for optimum activity of the enzyme.

Traditionally, heat treatment has been used to deactivate the residual enzyme in processes involving the use of enzymes. However, porcine pancreatin has another disadvantage because it is not fully deactivated by heat treatment, and even treatment of the enzyme at a temperature of 95° C. for 30 minutes may not sufficiently deactivate the residual enzyme. The use of a higher temperature is impossible in view of the sensitivity of the phospholipid and free fatty acids to heat.

FEMS Microbiol. Lett. 3(2), 85-7, Vol. 3, No. 2, 1978 discloses the detection of phospholipase A1 activity in various filamentous fungi, including Aspergillus strains, but there is no disclosure of the isolation and purification of the enzyme. Biological Abstracts, vol. 72, Philadelphia, Pa., Abstract No. 012592, discloses the purification and characterization of phospholipids by various phospholipases.

It is known from British patent specification GB-B-1,525,929 (Unilever) to treat phospholipoproteins or phospholipoprotein containing materials, such as egg yolk, whole egg, blood serum, wheat protein, soybean, and the like, with phospholipase A. The phospholipase A is also active when the phospholipid is complexed with protein. After the treatment with the phospholipase, the lysophospholipoprotein is formed. The lysophospholipid is complexed with a protein. The lysophospholipoprotein containing material disclosed in GB-B-1,525,929 has achieved considerable commercial success as an emulsion stabilizer, particularly in oil-in-water emulsions. They enabled the manufacture of sterilizable emulsions, which in practice turned out to be commercially very successful, because they had a long shelf life and an excellent creamy taste.

The following patents disclose subject matter which is related to or relevant to the subject invention.

Japanese Abstract No. 58212783 A2, Kyowa Hakko Kogyo Co. Ltd., discloses a process whereby a microorganism, e.g. *Streptomyces scabies* ATCC15485 or *Streptomyces achromogenes* variety *streptozoticus* NRRL2697, belonging to the genus Streptomyces, and having the ability to produce phospholipase A, is cultivated in a culture medium at 22° C. to 40° C. and a neutral or slightly alkaline pH for about 2 to 6 days. The phospholipase A is collected mainly from the culture fluid.

Japanese Abstract No. 06153939 A2, Snow Brand Milk Prod. Co. Ltd., discloses a process whereby an alga of the genus Euglena (preferably Euglena gracilis) having the ability to produce phospholipase A is cultured in a culture medium containing a carbon source (preferably glucose), a nitrogen source (preferably glutamic acid or diammonium hydrogenphosphate) at 4–35 ratio (C/N) under conditions of preferably pH 3.0–4.5, 20–32° C. culture temperature and irradiation with light or in the dark for 3–7 days, to produce and accumulate phospholipase A in the organism. The resultant phospholipase A is then separated and collected to provide the objective phospholipase A.

U.S. Pat. No. 5,521,080, Hattori et al., discloses a method for preparing a phospholipase A1 which comprises (a) culturing a phospholipase A1 producing strain of Aspergillus under conditions which allow for the production of the phospholipase A1; (b) after culturing, diluting the culture with water or an appropriate buffer solution; (c) filtering the resulting solution under pressure to remove any insoluble matter; and optionally (d) purifying the enzyme.

U.S. Pat Nos. 5,378,623 and 5,538,874, Hattori et al., are related and disclose a phospholipase A1 which is capable of hydrolyzing a phospholipid to produce a 2-acyl lysophospholipid and is obtainable from species of the fungus Aspergillus.

EP 0 575 133 B1, Sankyo Company Limited, discloses a phospholipase A1 obtainable from fungus selected from *Aspergillus niger* and *Aspergillus oryzae* characterized in that said phospholipase A1: (a) hydrolyzes phospholipid between about pH 2.5 and about pH 6.0; (b) has a molecular weight of between about 30,000 and about 40,000 daltons, as determined by sodium dodecyl sulphate polyacrylamide gel electrophoresis; (c) has a stability to temperature with an upper limit of between about 45 and about 90° C.; (d) has a pI under isoelectric point electrophoresis at about pH 2.8 to about pH 4.5; and (e) has an optimum temperature for activity of from about 30 to about 65° C.

U.S. Pat. No. 4,119,564, van Dam, discloses a process whereby oil-in-water emulsions with an increased viscosity are produced by incorporating an effective amount of phospholipase A-treated phospholipoprotein.

Related U.S. Pat. No. 4,034,124, van Dam, discloses emulsions comprising an oil phase, an aqueous phase and a phospholipoprotein which has been subjected to a treatment with phospholipase A as an emulsion stabilizer. These emulsions have an increased stability, especially heat stability, compared with emulsions which do not contain such a stabilizer.

U.S. Pat. No. 5,028,447, Schenk, discloses a process whereby oil and water emulsions which contain a phospholipoprotein material which has been modified by phospholipase A, and at least one native starch based thickening agent, are prepared by subsequently gelatinizing the thickening agent, incorporating the modified phospholipoprotein containing material into the gelatinized thickening agent, then incorporating the oil (which may at least partially be replaced by a low-calorie fat substitute) and finally homogenizing the mixture obtained. Canadian Patent No. 1,210,224 is related.

EP 0 319 064 B1, Unilever Nev., discloses a process for the preparation of a water and oil emulsion comprising a phospholipoprotein containing material, which has been modified by phospholipase A, and at least one native starch based thickening agent, which comprises: (a) at least partly gelatinizing the native starch based thickening agent; (b) incorporating the phospholipoprotein containing material, which has been modified by phospholipase A, into the gelatinized native starch based thickening agent; (c) incorporating from 5% to 85% by weight of oil or fat containing oil into the mixture obtained in step (b); and (d) homogenizing the final mixture obtained.

U.K. Patent No. 1,585,105, Unilever Limited, discloses an oil-in-water emulsion which contains a phospholipase A-treated phospholipoprotein having a degree of conversion of at least 55% and at least one thickening agent in a proportion which is less than that required for obtaining an emulsion of the same composition and viscosity but containing phospholipoprotein of a lower degree of conversion.

U.S. Pat. No. 5,082,674 and Canadian Patent No. 2,026,447, Carrell et al., disclose a process for the manufacture of a lysophospholipoprotein-comprising foodstuff. The dried lysophospholipoprotein or dried lysophospholipoprotein-comprising material, preferably having a moisture content of at most 10 wt %., at a level of 0.1–90 wt. % therein, is used as a texture-modifying agent, a glossing agent, a freeze-thaw stabilizing agent, a heat-stabilizing agent and a syneresis-inhibiting agent.

U.S. Pat. No. 5,314,706, Colarow et al., discloses an egg yolk fortified with exogenous soybean lysophosphatidylcholine contained in exogenous soybean lysophospholipids which is employed as an emulsification agent in oil and water emulsions, particularly in emulsions which are sterilized. The agent may be obtained by hydrolyzing phospholipids derived from soybeans with phospholipase A2, deactivating the phospholipase A2 with a proteolytic enzyme and then inactivating the proteolytic enzyme by heat-treatment at a temperature of from 80° C. to 90° C. Egg yolk is fortified by combining and homogenizing the so-obtained lysophospholipids, or exogenous phospholipids containing lysophosphatidylcholine.

U.S. Pat. No. 5,750,164, Saito et al., discloses a method of decreasing cholesterol concentration in eggs, processed egg foodstuffs, meat, fish meat, dairy products and processed foodstuffs thereof, which includes hydrolyzing phospholipids in the eggs or processed egg foodstuffs or other products with one member selected from the group of phospholipase $A_1$, $A_2$, B, D, lysophospholipase and a mixture thereof, and subjecting the phospholipid-hydrolyzed eggs or processed egg foodstuffs or other products to a conventional cholesterol-decreasing treatment.

Japanese patent Abstract No. 62262998 A2, QP Corp., discloses a process whereby a natural phospholipid-containing substance such as egg yolk is added with a phospholipase A2 preparation-containing material) (e.g. purified phospholipase A2 preparation originated from animal pancreas) to effect enzymatic reaction. The phospholipid in the substance is decomposed by the reaction to obtain a lysophospholipid containing material. The obtained lysophospholipid-containing material is dried at about s 80° C. by spray drying, etc., to powder having a water content of s 10%. The powder is extracted with a polar solvent such as ethanol to extract lysophospholipid. The solvent is distilled from the extract under reduced pressure to obtain the objective lysophospholipid-containing material composed of 68 wt. % neutral lipid and 32 wt. % phospholipid (30 wt. % thereof is lysophospholipid).

Japanese patent Abstract No. 63209742 A2, QP Corp., discloses a method whereby an emulsifier is prepared by mixing phospholipid, protein, phospholipase A2 and clean water uniformly in a mixer or a colloid mill, etc., treating at ca. 40° C. and drying if necessary. Suitable protein is albumin, globulin, gelatin, etc., and suitable proportion of protein to be present in aqueous suspension of phospholipid is 1:(ca 0.5 to 2) phospholipid to protein. The phospholipase A2 is an enzyme for hydrolyzing the fatty acid ester moiety at the middle part of a glyceride constituting the phospholipid, and the amount thereof to be used is ca. 0.1 to 5 wt. % based on the amount of the phospholipid.

U.S. Pat. No. 5,213,968, Castle et al., discloses a process whereby emulsifying agents are prepared by sequentially treating a biological material with a protease and a lipase. The enzymatically treated biological material may be pasteurized during or following the enzymatic treatment.

EP 0 414 024 B1, Societe des Produits Nestle S.A., discloses a process for the preparation of an emulsifying agent which comprises treating a biological material containing a lipid as well as a lipoprotein and/or a protein with a protease and a lipase and pasteurizing the product. The treatment with the protease and the lipase is carried out sequentially in any order.

SUMMARY OF INVENTION

The present invention relates to a process for the manufacture of lysophospholipoprotein-comprising foodstuffs, such as sauces, spreads, mayonnaise, dressings, soups, bakery products, creamers, creamer-thickeners, ice cream, drinks, dairy products, desserts, sherbets, meals, and combinations thereof, with no detectable amylase (and protease) activity.

The invention is directed to a process for the manufacture of a liquid egg yolk product containing lysophospholipoprotein comprising: (a) processing a phospholipase A-containing microbial fermentate to remove undesirable-amylase and protease co-products of the fermentation to produce a refined phospholipase A-containing microbial product; and (b) combining a liquid egg yolk with the refined phospholipase A-containing microbial product of step (a) to produce a modified liquid egg yolk product containing lysophospholipoprotein, said modified liquid egg yolk product having (i) a degree of conversion of phospholipoprotein to lysophospholipoprotein of at least 10%; and (ii) an amylase activity of less than 50 units/litre.

The phospholipase A-containing fermentate of step (a) can be produced by a fermentation of a phospholipase A-producing microorganism in a nutrient medium. Suitable prior art phospholipase A producing microorganisms can be used in the invention but a preferred microorganism can be *Streptomryces violaceoruber* or a genetically modified *Thermontyces lanuginous/Fusarium oxysporun*. Step (a) can be conducted at a temperature below about 20° C. and at a pH between about 4.9 and 5.2.

The undesirable amylase and protease co-products can be removed in step (a) by passing the fermentate through a cross-flow dialysis apparatus having a PES 50K membrane.

The liquid egg yolk product containing lysophosphoprotein can have a phospholipase activity of less than 250 units/litre. The liquid egg yolk product containing lysophospholipoprotein can have a protease activity of less than 0.01 fluorescence units/mi/min.

The invention is also directed to a product prepared according to the process of the invention. The product can contain up to 20% added salts, and up to 50% added carbohydrates, including sugar, malto-dextrin, glucose or corn syrup solids. The product can contain up to 75% added liquid egg albumin or concentrated liquid egg albumin.

The product can be spray dried at an inlet temperature of from about 200° C. to about 250° C. and an air outlet temperature from about 75° C. to about 100° C. so that the final moisture of the dried product is less than about 10% by weight.

The product can be incorporated into an emulsion of oil, water, vinegar, starch, sugar and salt. The emulsion can include egg yolk.

DRAWINGS

In drawings which illustrate specific embodiments of the invention, but which should not be construed as restricting the spirit or scope of the invention in any way.

DETAILED DESCRIPTION OF SPECIFIC EMBODIMENTS OF THE INVENTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense. Applicable knowledge in the prior art is incorporated herein by reference.

Over the years, the food industry has evolved to a point where all ingredients used in common food products such as sauces, spreads, mayonnaise, starch-based salad dressings, oil-water based salad dressings, soups, bakery products, creamers, creamer-thickeners, ice cream, drinks, dairy products, desserts, sherbets, and the like, must be of kosher quality, that is, not derived from porcine sources. Furthermore, with the frequent recurrence of foot and mouth disease in cattle and the "mad cow" disease problem prevalent in cattle in Great Britain, a strong phobia has developed in the food industry to the use of components that are derived from bovine sources. There is a strong need in the food industry for an emulsifier which is not derived from porcine or bovine sources, which can be used in oil-water and water-oil emulsions, which can withstand changes in pH level, which has long shelf life, and which can withstand a wide variation in temperatures.

The emulsions prepared according to the invention can have either the oil phase or the aqueous phase as the continuous phase, and are in this specification referred to as water-in-oil emulsions and oil-in-water emulsions, respectively. Oil-in-water emulsions are preferred. The latter type of emulsion means for the purpose of this specification continuous aqueous phases containing any amount of fat and/or oil in dispersed form. Examples of emulsions which come under this definition are edible products like phase inversion margarines, soups or sauces, natural or artificial fruit juices, mayonnaise, dressings or spreads.

Examples of phospholipoprotein-containing substances are casein, skim milk, buttermilk, whey, cream, soyabean, yeast, egg yolk, whole egg, blood serum and wheat proteins. Egg yolk is used preferably as source of the phospholipoprotein. Egg yolk or other sources of phospholipoprotein can be subjected to the action of phospholipase A and the modified product is then incorporated in the products according to the invention.

The inventors herein have invented a novel liquid amylase-free egg yolk product containing lysophospholipoprotein, which is not derived from animal sources, notably porcine or bovine sources. The inventors have also invented a process for manufacturing a liquid egg yolk product containing lysophospholipoprotein.

The inventors have prepared a process for the manufacture of a liquid egg yolk product comprising lysophospholipoprotein which comprises: (a) processing a fermentation of a microorganism in a nutrient medium which produces microbial phospholipase A to remove undesirable amylase and protease co-products of the fermentation to produce a refined microbial phospholipase A product; and (b) modifying a liquid egg yolk with the refined microbial phospholipase A to produce a modified liquid egg yolk product which contains lysophospholipoprotein, the modified liquid egg yolk product comprising lysophospholipoprotein having a degree of conversion of phospholipoprotein to lysophospholipoprotein of at least 10% and an amylase activity of less than 50 units per litre. Advantageously, the process produces a modified liquid egg yolk product containing lysophospholipoprotein which has a degree of conversion of phospholipoprotein to lysophospholipoprotein of at least 50%.

A problem with most methods of producing phospholipase A by microbial fermentation is that high levels of amylase are obtained as a by-product. Protease is also produced as a byproduct. High levels of amylase are undesirable because the amylase breaks down starch into undesirable products. Many food products are starch-based and hence significant levels of amylase in a food additive cannot be tolerated because the amylase leads to breakdown of the starch base. Significant protease levels are also to be discouraged since the protease tends to react with egg white and other proteins and cause water in the oil-water emulsions to begin to separate.

The inventors have discovered a method and processing equipment which enables the amylase to be separated from the microorganism produced phospholipase A fermentation medium so that the amylase activity in the end product is basically non-existent. Amylase activities of less than 50 units per litre have been obtained. The system according to the invention uses a specific dialysis procedure for separating the amylase and the protease from the crude phospholipase A medium. The inventors have tested and rejected a large number of different dialysis machines in an effort to discover a feasible method for separating amylase from the crude phospholipase A fermentation medium. None were found to be satisfactory for purposes of the invention. The inventors have now found a dialysis system available from North Carolina SRT under the model number NCSRT UF with a PES 50K membrane, or smaller, capable of separating the amylase and protease from the phospholipase A.

For purposes of the invention, the inventors have found that a suitable microbial fermentation product containing phospholipase A is available from Genencor. One type of phospholipase A microorganism fermentation product that can be used in the process according to the invention is a *Streptonyces viola ceoruber* derived product available from Genercor. Another microorganism that can be used in the process is a genetically modified *thermomyces lanuginous/Fusarium oxysporum* produced by submerged fermentation and available from Novozymes. Other suitable microbial phospholipase A products may be suitable for purposes of the invention, including one or more of the phospholipase A-containing products referred to in the Background. The key to the subject invention is that the inventors have discovered a method and apparatus for reducing the amylase and protease concentrations of the crude microbial enzyme products available from commercial sources so that the amylase and protease activity are reduced to insignificant levels.

The following is a detailed discussion of the apparatus and steps the inventors have discovered which enable them to successfully separate amylase and protease from the phospholipid A-containing material.

Standard Operation Procedure for Separating Amylase and Protease from Crude Microorganism Produced Phospholivase A Prefiltration of the crude enzyme solution: The crude enzyme solution should be prefiltered through a 5 micron or less filter.

Stage One Dialysis

The following ingredients are used: kosher sodium citrate; kosher citric acid; crude enzyme (obtained from Genencor) approx. 100 lbs. (45L); and RO purified water. The following equipment is used: an NCSRT UF system with PES 50K membrane module for dialysis stage. Any other type of suitable tangential flow or spiral wound membrane system with a similar membrane type can be used.

Method of Preparation:

(1) Prepare approximately 2 to 6 volumes of citrate buffer at pH 4.8 to 5.2.

(2) Load the crude enzyme into feed tank. Collect a sample from the tank for testing.

(3) Start the dialysis system by setting flow rates so that the flux (litres/m$^2$ hour) is approximately 2 to 10 LMH and adjust the back pressure valve to between 0 to 20 psi on the retentate exit line of the membrane. Collect the permeate in pail(s) or a suitable receiver tank (150 to 200L). The permeate line flows should not be blocked or build up significant back pressure.

(4) Start the citrate buffer flow and set it to match the permeate flow into the feed tank. For a 1 meters membrane at 7 LMH, approximately 150 (7*1) or 21.4 hours will be required to dialyse the enzyme through the membranes and into the permeate.

(5) Once all the buffer has been pumped into the feed tank, the system should be allowed to continue to operate until the volume in the feed tank has been reduced to approximately 10 to 20L.

(6) Shut the process down and collect from the system and feed tank all remaining material into containers.

Stage Two

A stage two procedure is used to concentrate the product, when required. The following ingredients are used: 150 to 200L of collected PA2 Permeate from Stage One; and RO purified water. The following equipment is required: NCSRT UF system with a 10K or 5K membrane module for the concentration stage (or other suitable tangential flow or spiral wound membrane systems).

Method of Preparation:
(1) Provide sufficient cooling to the unit to keep the enzyme in the feed tank below 20° C., preferably at 10° C., if possible.
(2) Load the dialysed enzyme (PA2 Permeate from Stage One) into the feed tank. Collect a sample from the tank for analysis.
(3) Start the concentration system by setting flow rates (cross flow of 20 to 100 L/min.) so that the flux is in the range of 5 to 60 LMH and adjust the back pressure valve to generate between 10 to 100 psi on the retentate exit line of the membrane.
(4) Reduce the volume in the feed tank to approximately 10 to 20 L (or less if care is taken to prevent air entrainment and turbulence). This will take approximately 5 to 20 hours to complete.
(5) Shut the system down and collect the remaining material from the system and feed tank.

Figure 2:
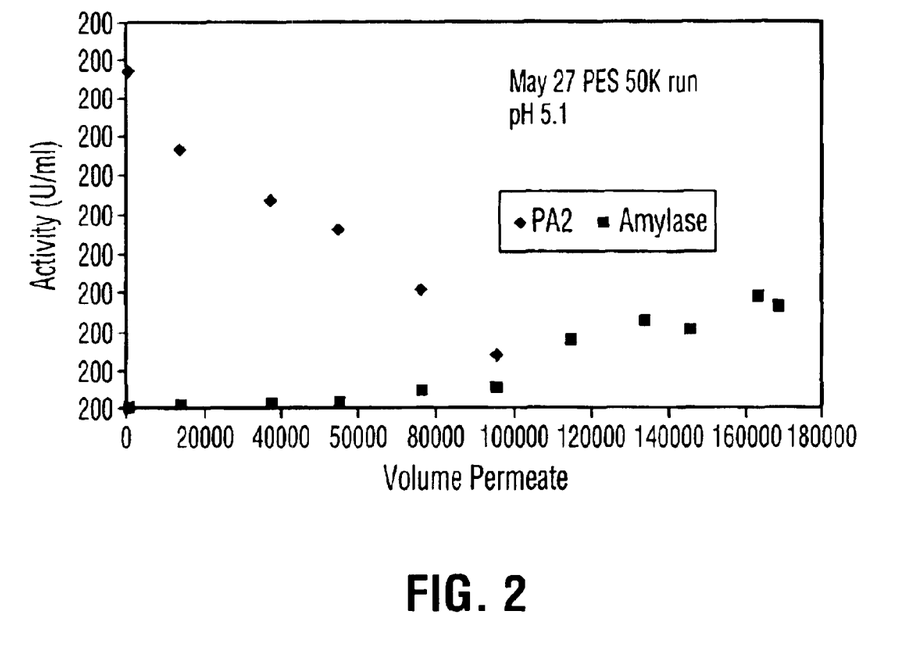
FIG. 2 illustrates a plot of the amount of phospholipase A passing in the permeate and amylase concentrating in the retentate after passing a phospholipase A and amylase fermentator through a dialysis filter having a PES 50K membrane.

FIG. 2 illustrates a plot of the amount of phospholipase A passing in the permeate and amylase concentrating in the retentate after passing a phospholipase A and amylase fermentator through a dialysis filter having a PES 50K membrane.

Standard Operating Procedure for Producing Modified Liquid Egg Yolk Products Containing Lysophospholipoprotein from Refined Amylase and Protease-Free enzyme Product Obtained from the Stage One Dialysis or the Stage Two Concentration
(1) Prepare liquid salt yolk in churn.
(2) Prepare alkaline base solution.
(3) Adjust batch initial pH.
(4) Adjust yolk temperature.
(5) Add enzyme.
(6) Perform hydrolysis step and add alkaline base as necessary.
(7) Terminate hydrolysis.
(8) Pasteurize.
(9) Package.

Figure 1:
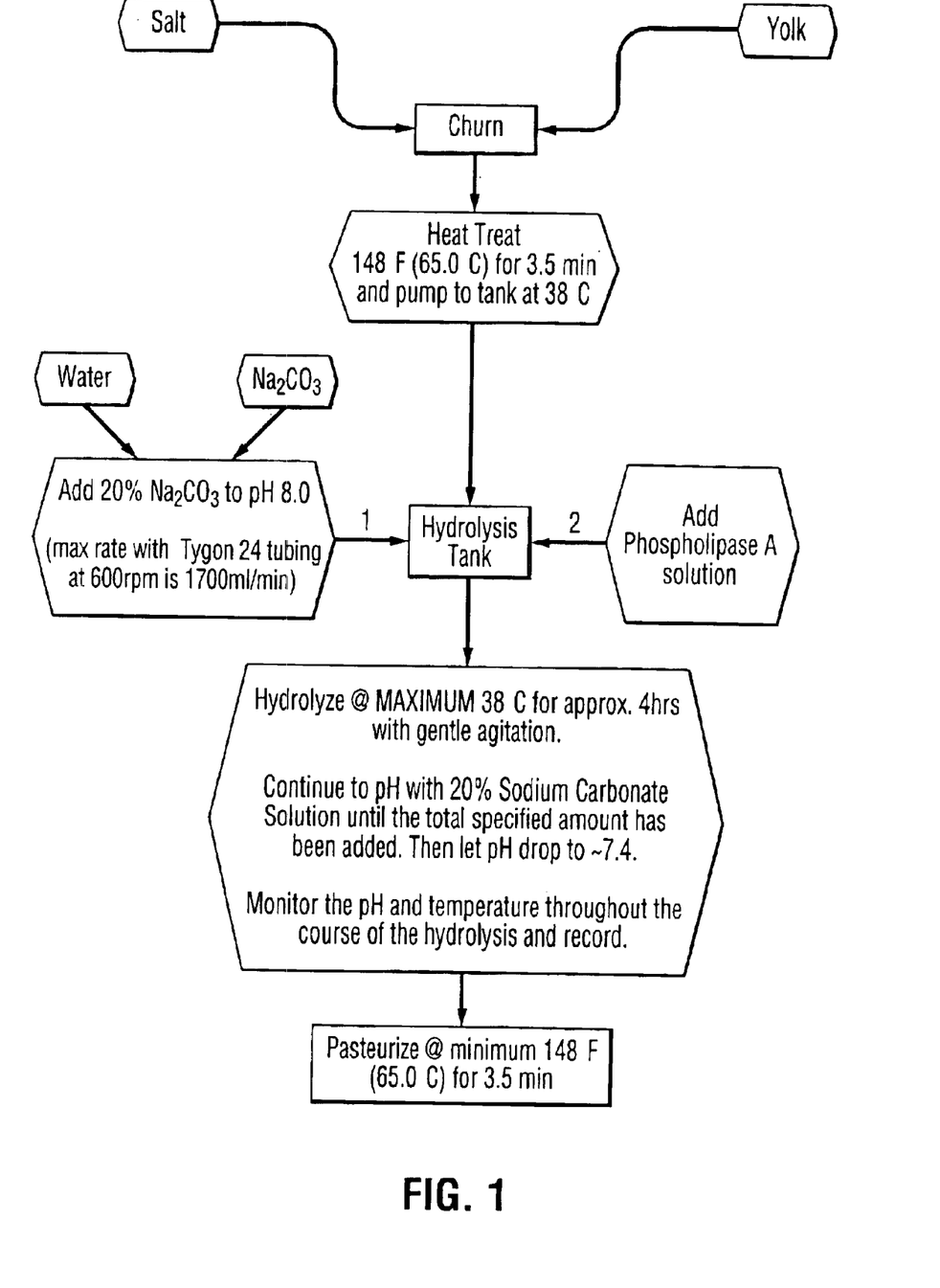
FIG. 1 illustrates a schematic flow sheet of a process for modifying liquid egg yolk with refined phospholipase A to produce a modified egg yolk product containing lysobospholipoprotein.

FIG. 1 illustrates a schematic flow sheet of a process for modifying liquid egg yolk with refined phospholipase A to produce a modified egg yolk product containing lysophospholipoprotein.

Figure 6:
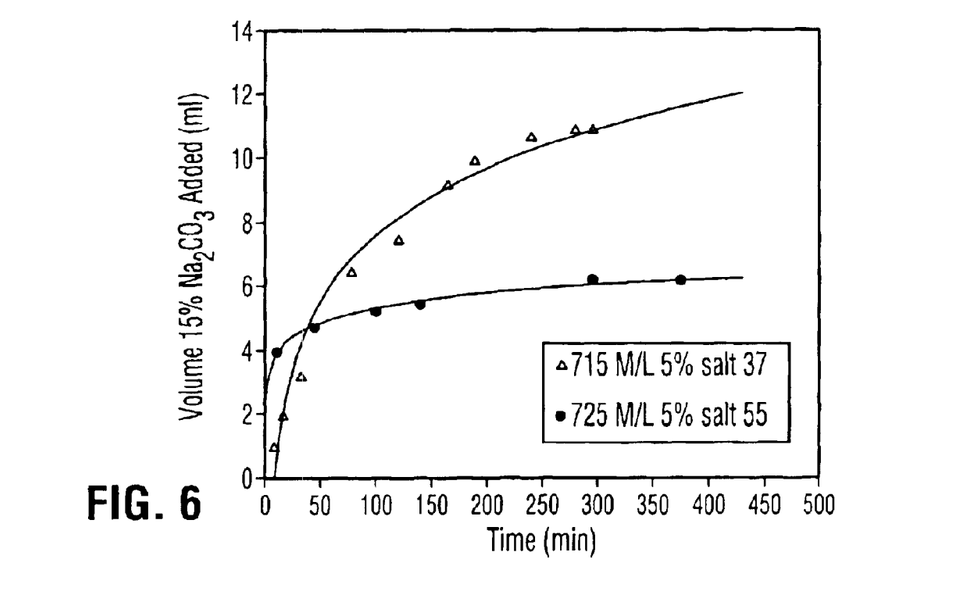
FIG. 6 illustrates a plot of volume over time of soda ash added to yolk to maintain constant pH at different temperatures.

FIG. 6 illustrates a plot of volume over time of soda ash added to yolk to maintain constant pH at different temperatures.

The following is a recipe of a typical starch thickened oil-water emulsion salad dressing incorporating a liquid egg yolk product according to the invention.

| Ingredients | (/g) |
|---|---|
| Water | 159.9 |
| Vinegar | 170.0 |
| Starch | 30.0 |
| Sugar | 105.5 |
| Salt | 11.0 |
| Water | 190.2 |
| Salt | 8.5 |
| Enzyme modified yolk | 25.0 |
| Vegetable oil | 300.0 |
| Total | 1000.0 |

Figure 3:
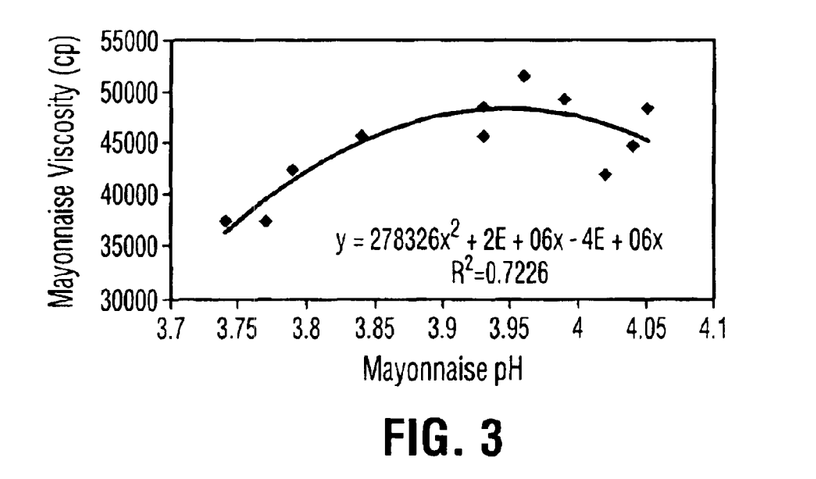
FIG. 3 illustrates a plot of effect of mayonnaise pH on mayonnaise viscosity.

FIG. 3 illustrates a plot of effect of mayonnaise pH on mayonnaise viscosity.

Figure 4:
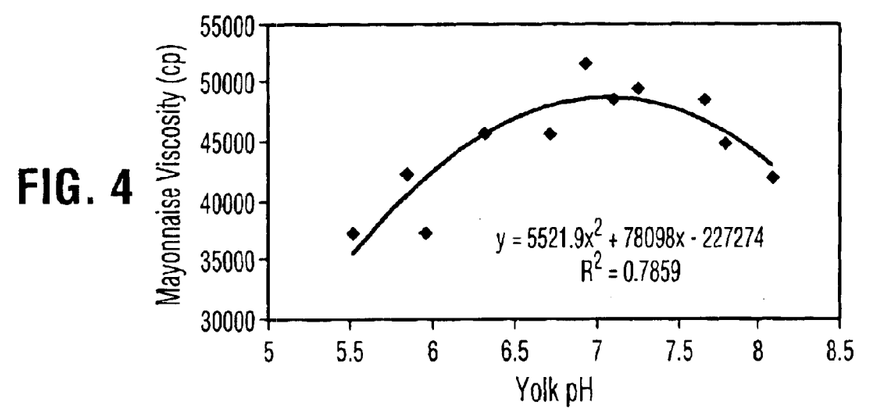
FIG. 4 illustrates a plot of the effect of enzyme modified yolk pH on mayonnaise viscosity.
Figure 5:
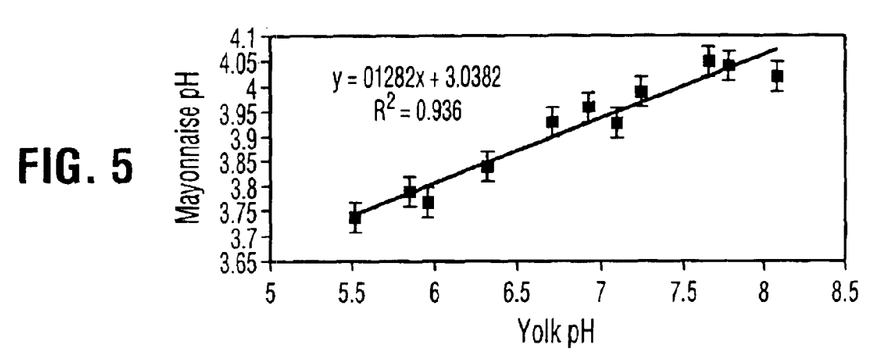
FIG. 5 illustrates a combination of FIGS. 3 and 4 and represents a plot of the effect of enzyme modified yolk pH on mayonnaise pH.

FIG. 4 illustrates a plot of the effect of enzyme modified yolk pH on mayonnaise viscosity. FIG. 5 illustrates a combination of FIGS. 3 and 4 and represents a plot of the effect of yolk pH on mayonnaise pH.

Figure 7:
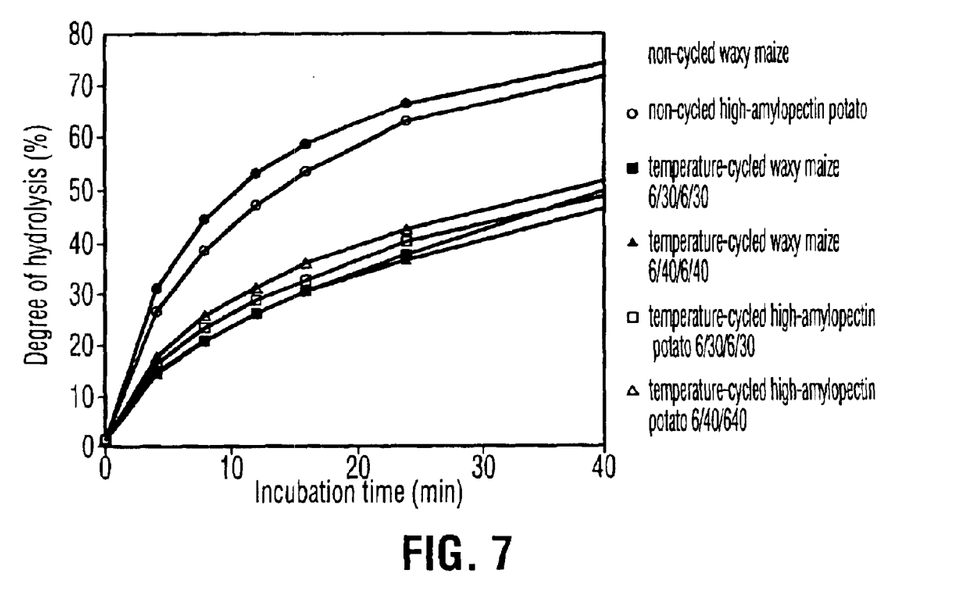
FIG. 7 illustrates a plot of hydrolysis of starch samples after different incubation times with porcine pancreatic 2-amylase.

FIG. 7 illustrates a plot of hydrolysis of starch samples after different incubation times with porcine pancreatic 2-amylase.

Figure 8:
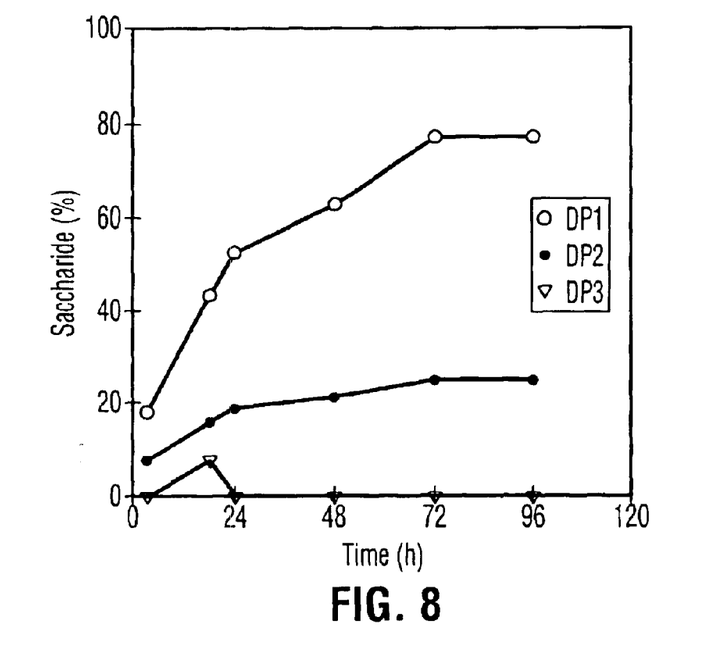
FIG. 8 illustrates a plot of time course of saccharide formation of *A. pullulans* amylase preparation from maltodextrin DE.
Figure 9A:
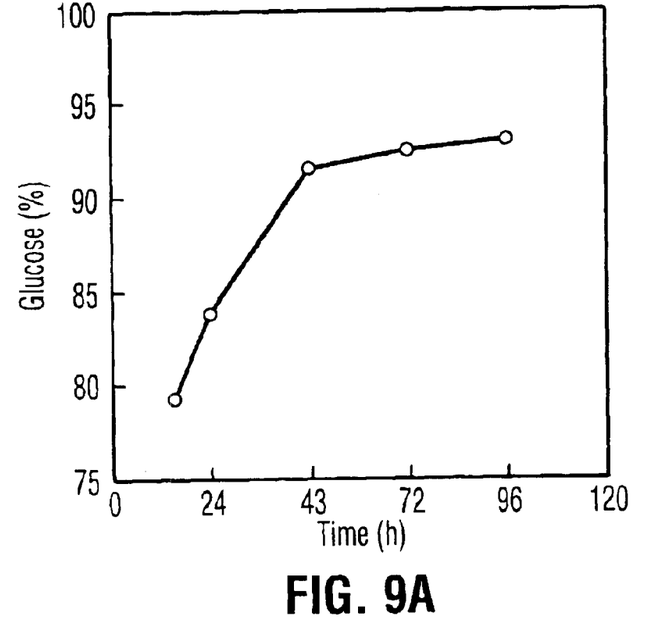
FIGS. 9A and 9B illustrates plots of time course of glucose production of *A. pullulans* amylase preparation from maltodextrin (A) and cornstarch (B).
Figure 9B:
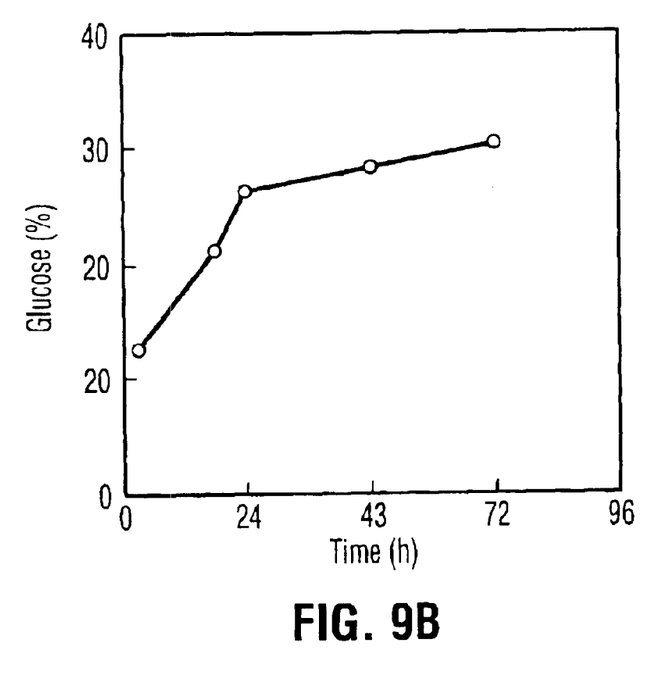
Figure 10:
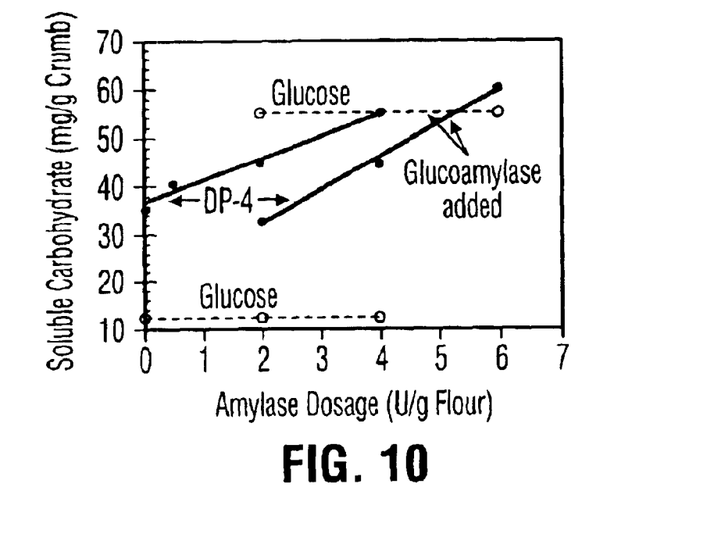
FIG. 10 illustrates plots of production of soluble carbohydrate in white bread with Aspergillus intermediate temperature stability enzyme.

FIG. 8, illustrates a plot of time course of saccharide formation of $A.\ pullulans$ amylase preparation from maltodextrin DE. FIGS. 9A and 9B illustrate plots of time course of glucose production of $A.\ pullulans$ amylase preparation from maltodextrin (A) and cornstarch (B). FIG. 10 illustrates plots of production of soluble carbohydrate in white bread with Aspergillus intermediate temperature stability enzyme.

Figure 11:
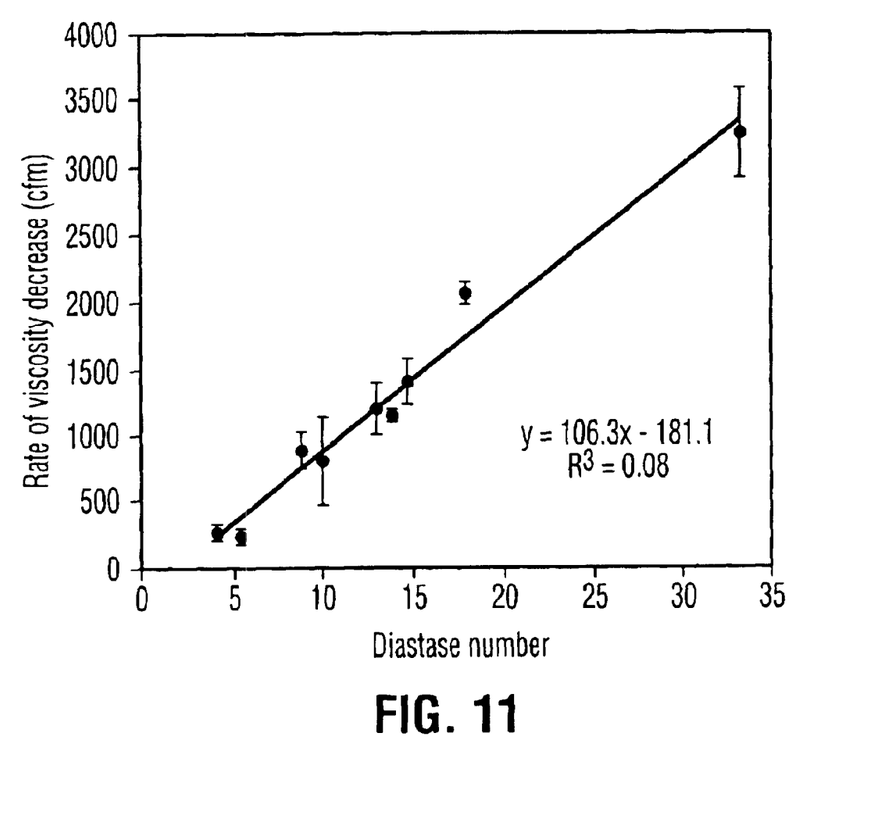
FIG. 11 illustrates a plot of the relationship between the rate of starch viscosity decrease with honey.
Figure 12:
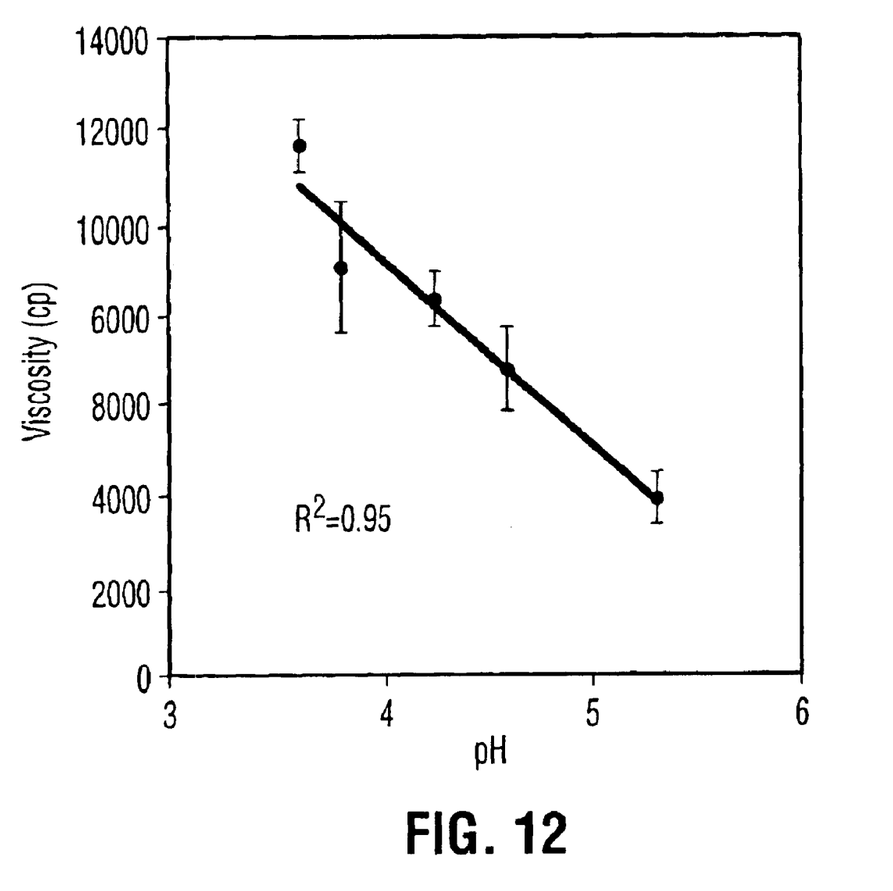
FIG. 12 illustrates a plot of the effect of pH on honey amylase catalyzed degradation of unmodified waxy maize starch at different pH values.

FIG. 11 illustrates a plot of the relationship between the rate of starch viscosity decrease with honey. FIG. 12 illustrates a plot of the effect of pH on honey amylase catalyzed degradation of unmodified waxy maize starch at different pH values.

The following table illustrates recommended amylase activity for starch thickened dressing shelf stability.

| | Starch Thickened Dressing Shelf Stability | | | | | | | | | | |
|---|---|---|---|---|---|---|---|---|---|---|---|
| | Novo HI Recommendation | | Novo LO Recommendation | | MFI Current Use | | IEP LO Level Use | | Purified Enzyme | | Novo Porcine Control |
| Amylase Activity | 20 | | 20 | | 20 | | 20 | | 3.33 | | 0 |
| PA2 Activity | 300 | | 300 | | 300 | | 300 | | 1800 | | 11175 |
| Units Activity per kg | 50000 | | 10000 | | 1000 | | 500 | | 500 | | 500 |
| Yolk | 1000 | | 1000 | | 1000 | | 1000 | | 1000 | | 1000 |
| Enzyme | 166.667 | 0.140 | 33.333 | 0.028 | 3.333 | 0.003 | 1.667 | 0.001 | 0.278 | 0.000 | 0.045 0.000 |
| 2% Salt Yolk | 1020.408 | 0.860 | 1020.408 | 0.860 | 1020.408 | 0.860 | 1020.408 | 0.860 | 1020.408 | 0.860 | 1020.408 0.860 |
| Sub Total | 1187.075 | | 1053.741 | | 1023.741 | | 1022.075 | | 1020.686 | | 1020.453 |
| Water | 0.000 | 0.000 | 133.333 | 0.112 | 163.333 | 0.138 | 165.000 | 0.139 | 166.389 | 0.140 | 166.622 0.140 |

-continued

Starch Thickened Dressing Shelf Stability

|  | Novo HI Recommendation | | Novo LO Recommendation | | MFI Current Use | | IEP LO Level Use | | Purified Enzyme | | Novo Porcine Control | |
| --- | --- | --- | --- | --- | --- | --- | --- | --- | --- | --- | --- | --- |
| Total | 1187.075 | 1.000 | 1187.075 | 1.000 | 1187.075 | 1.000 | 1187.075 | 1.000 | 1187.075 | 1.000 | 1187.075 | 1.000 |
| Total Units Amylase | 2808.02 | | 561.60 | | 56.16 | | 28.08 | | 0.78 | | 0.00 | |
| Amylase Testing | 0.392063 | | 0.381954 | | 0.37968 | | 0.379553 | | 0.379448 | | 0.37943 | |
| Yolk/Enzyme/Water Mix | 10 | | 10 | | 10 | | 10 | | 10 | | 10 | |
| Water | 50 | | 50 | | 50 | | 50 | | 50 | | 50 | |
| Solids | 0.0653438 | | 0.063659 | | 0.06328 | | 0.063259 | | 0.063241 | | 0.063238 | |

The following table illustrates a recipe for a typical mayonnaise incorporating the liquid egg yolk product according to the invention.

| Ingredients | (/g) | (/%) |
| --- | --- | --- |
| Whole Egg 35% solids | | |
| Enzyme modified egg yolk product | 42.9 | 5.72 |
| Sugar | 4.0 | 0.53 |
| Salt | 6.9 | 0.91 |
| 5% Vinegar | 56.3 | 7.51 |
| Canola Oil #1 | 127.5 | 17.00 |
| Canola Oil #2 | 450.0 | 60.00 |
| Water | 62.5 | 8.33 |
| Total | 750.0 | 100.0 |

Colorimetric Method for Testing for Presence of α-Amylase in Egg Application and Principle This method of testing for presence of amylase in egg has been developed by the inventors. The reducing groups, maltose and glucose, liberated from starch hydrolysis reduce 3,5-dinitrosalicylic acid, resulting in the formation of a colored product which can be measured spectrophotometrically at 560 nm.

Reagents (1) 0.02 M sodium phosphate buffer, pH 6.9 containing 0.006 M sodium chloride.

(2) 2.0 M sodium hydroxide.

(3) Dinitrosalicylic acid color reragent. Dissolve 1.0 g 3,5-dinitrosalicylic acid in 20 ml 2 M NaOH. Add slowly 30.0 g sodium potassium tartrate tetrahydrate. Dilute to a final volume of 100 m with distilled water. Store in a tightly sealed container and protect from $CO_2$. Stable for 2 weeks.

(4) 1% starch. Dissolve 1.0 g of soluble starch in 100 ml 0.02M sodium phosphate buffer, pH 6.9, containing 0.006M NaCl. Bring to a gentle boil to dissolve. Cool and make volume up to 100 ml, with distilled water, if necessary. Incubate at 25° C. for 5 minutes prior to assay.

(5) Enzyme (α-amylase) standards. Dilute to a concentration of 0.01 to 10 u/ml. Prepare 10 different concentrations within this range for a standard curve (eg. 10, 5, 2.5, 1.25, 0.625, 0.3125, 0,1563, 0.0781, 0.0391 u/nm).

Egg Samples (1) Measure 0.500 g of liquid egg yolk (or 0.250 g dried egg yolk, 0.500 g liquid egg white, 0.100 g dried egg white) into a 1.5 ml Eppendorf tube.

(2) Bring to 1.00 g with NaP buffer (prepared above).

(3) Vortex mixture until the egg and buffer are sufficiently mixed.

(4) Prepare dilutions of this mixture in 1.5 ml Eppendorf tubes. Dilute 2x, 10x, 20x and 50x.

(5) Centrifuge all tubes at 10,000 rpm for 20 minutes. Do not resuspend. Supernatant will be used as sample.

Procedure (1) Pipette 0.030 ml of each of the standard solutions in triplicate as shown on the plate layout. Use 0.030 mi of NaP buffer as a blank.

(2) Pipette 0.030 ml of each sample dilution supernatant, in duplicate, into the plate.

(3) Add 0.030 ml of starch solution to all wells and place lid on microtitre plate. Tap gently to mix.

(4) Incubate plate at 37° C. for 25 minutes on Elisa plate incubator.

(5) Turn on hot plate and boil water (use boiling chips!!) about 0.5–0.75cm deep in a Pyrex dish.

(6) After 25 minutes of incubation, add 0.060 ml of 2,5-dinitrosalicylic acid color reagent to all wells. Tap gently to mix.

(7) Cover plate with stick-on type microtitre plate cover and place in Pyrex dish with boiling water.

(8) Heat for 5 minutes to develop color.

(9) Let plate cool to room temperature in a shallow dish of cold water.

(10) Remove stick-on cover and add 0.120 ml $dH_2O$ to each well in plate. Tap gently to nix.

(11) Read plate in Multiskan using amylase protocol (measure @ 560 nm).

Calculations (1) Plot standard curve in Excel.

(2) Remove data points that are out of range (on high end the absorbance values will plateau, generally at ABS >3.1) and add a linear best-fit trend line.

(3) Average duplicate data for samples and calculate α-amylase activity based on value from standard curve.

(4) Multiply by dilution factor to obtain result in u/ml. Multiply again by w/w dilution factor 0.500 g/1.000 g (for liquid yolk) to obtain result in u/g.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A process for the manufacture of a liquid egg yolk product containing lysophospholipoprotein comprising:

(a) processing a phospholipase A-containing microbial fermentate to remove amylase and protease co-products of the fermentation to produce a refined phospholipase A-containing microbial product; and (b) combining a liqued egg yolk with the refined phospholipase A-containing microbial product of step (a) to produce a modified liqued egg yolk product containing lysophospholipoprotein, said modified liquid egg yolk product having
   (i) a degree of conversion of phospholipoprotein to lysophospholipoprotein of at least 10%; and
   (ii) an amylase activity of less than 50 units/litre.

2. The process of claim 1 wherein the phospholipase A-containing fermentate of step (a) is produced by a fermentation of a phospholipase A-producing microorganism in a nutrient medium.

3. The process of claim 2 wherein the microorganism is *Streptomyces violaceoruber* or a genetically modified *Thermonyces lanuginous/Fusarum oxysporum.*

4. The process of claim 1 wherein step (a) is conducted at a temperature below about 20° C.

5. The process of claim 1 wherein step (a) is conducted at a pH between about 4.9 and 5.2.

6. The process of claim 1 wherein the amylase and protease co-products are removed in step (a) by passing the fermentate through a cross-flow dialysis apparatus having a PES 50K membrane.

7. The process of claim 1 wherein the liquid egg yolk product containing lysophosphprotein has a phospholipase activity of less than 250 units/litre.

8. The process of claim 1 wherein the liquid egg yolk product containing lysophospholipoprotein has a protease activity of less than 0.01 fluorescence units/ml/min.

9. The process of claim 7 wherein the liquid egg yolk product containing lysophospholipoprotein has a protease activity of less than 0.01 fluorescence units/ml/min.

10. A product prepared according to the process of claim 1.

11. A product prepared according to the process of claim 2.

12. A product prepared according to the process of claim 3.

13. A product prepared according to the process of claim 4.

14. A product prepared according to the process of claim 5.

15. A product prepared according to the process of claim 6.

16. A product prepared according to the process of claim 7.

17. A product prepared according to the process of claim 8.

18. A product prepared according to the process of claim 9.

19. A product prepared according to claim 10 containing up to 20% added salts.

20. A product prepared according to claim 10 containing up to 50% added carbohydrates.

21. A product prepared according to claim 10 containing up to 20% added salts and up to 50% added carbohydrates.

22. A product prepared according to claim 10 containing up to 75% added liquid egg albumin or concentrated liquid egg albumin.

23. A product prepared according to claim 22 containing up to 20% added salts.

24. A product prepared according to claim 22 containing up to 50% added carbohydrates.

25. A product prepared according to claim 22 containing up to 20% added salts and up to 50% added carbohydrates.

26. A product prepared according to claim 10 spray dried at an inlet temperature of from about 200° C. to about 250° C. and an air outlet temperature from about 75° C. to about 100° C. so that the final moisture of the dried product is less than about 10% by weight.

27. A product prepared according to claim 10 spray dried at an inlet temperature of from 200° C. to 250° C. and an air outlet temperature from 75° C. to 100° C. so that the final moisture of the dried product is less than 10% by weight.

28. A product prepared according to claim 11 spray dried at an inlet temperature of from 200° C. to 250° C. and an air outlet temperature from 75° C. to 100° C. so that the final moisture of the dried product is less than 10% by weight.

29. A product prepared according to claim 12 spray dried at an inlet temperature of from 200° C. to 250° C. and an air outlet temperature from 75° C. to 100° C. so that the final moisture of the dried product is less than 10% by weight.

30. A product prepared according to claim 13 spray dried at an inlet temperature of from 200° C. to 250° C. and an air outlet temperature from 75° C. to 100° C. so that the final moisture of the dried product is less than 10% by weight.

31. A product prepared according to claim 14 spray dried at an inlet temperature of from 200° C. to 250° C. and an air outlet temperature from 75° C. to 100° C. so that the final moisture of the dried product is less than 10% by weight.

32. A product prepared according to claim 15 spray dried at an inlet temperature of from 200° C. to 250° C. and an air outlet temperature from 75° C. to 100° C. so that the final moisture of the dried product is less than 10% by weight.

33. A product prepared according to claim 16 spray dried at an inlet temperature of from 200° C. to 250° C. and an air outlet temperature from 75° C. to 100° C. so that the final moisture of the dried product is less than 10% by weight.

34. A product prepared according to claim 17 spray dried at an inlet temperature of from 200° C. to 250° C. and an air outlet temperature from 75° C. to 100° C. so that the final moisture of the dried product is less than 10% by weight.

35. A product prepared according to claim 18 spray dried at an inlet temperature of from 200° C. to 250° C. and an air outlet temperature from 75° C. to 100° C. so that the final moisture of the dried product is less than 10% by weight.

36. An emulsion of oil, water, vinegar, starch, sugar and salt, comprising a product prepared according to claim 10.

37. An emulsion prepared according to claim 36 further comprising egg yolk.

* * * * *